United States Patent [19]

Buckley

[11] 4,287,769
[45] Sep. 8, 1981

[54] APPARATUS AND METHOD WHEREBY WAVE ENERGY IS CORRELATED WITH GEOMETRY OF A MANUFACTURED PART OR THE LIKE OR TO POSITIONAL RELATIONSHIPS IN A SYSTEM

[75] Inventor: Bruce S. Buckley, Cambridge, Mass.

[73] Assignee: Massachusetts Institute of Technology, Cambridge, Mass.

[21] Appl. No.: 56,577

[22] Filed: Jul. 11, 1979

Related U.S. Application Data

[60] Continuation-in-part of Ser. No. 911,622, Jun. 1, 1978, Pat. No. 4,200,921, which is a division of Ser. No. 679,262, Apr. 22, 1976, Pat. No. 4,095,475.

[51] Int. Cl.³ .......................................... G01N 29/00
[52] U.S. Cl. ........................................ 73/627; 73/628
[58] Field of Search ...................... 73/627, 547, 628; 367/99, 108

[56] References Cited

U.S. PATENT DOCUMENTS

| | | | |
|---|---|---|---|
| 2,618,468 | 11/1952 | McConnell | 73/597 |
| 3,060,421 | 10/1962 | Rideout | 73/615 |
| 3,090,224 | 5/1963 | Rankin | 73/615 |
| 3,554,014 | 1/1971 | Berg et al. | 73/628 |
| 3,741,003 | 6/1973 | Gunkel | 73/637 |
| 4,095,475 | 6/1978 | Buckley | 73/628 |

Primary Examiner—Anthony V. Ciarlante
Attorney, Agent, or Firm—Arthur A. Smith, Jr.

[57] ABSTRACT

A way of automatically inspecting a machined part, for example, to a tolerance of 0.001 inches. A minicomputer monitors a change in phase of acoustic wave energy impinging upon a sample part and compares it with a change in phase of such energy for a standard or master part, any difference between the monitored changes being interpreted to determine if the sample is within acceptable tolerance limits. The inspection approach described uses no moving parts and can be used to inspect many dimensions of a part simultaneously in less than a second. Acoustic wave energy can be used to inspect parts of any shape. The inspection system disclosed can be used, as well, to monitor the geometry of an object over time to note any changes in said geometry. And the concepts of the inspection system can be employed in conjunction with robot-controlled devices to provide close-positioning data for such devices.

9 Claims, 5 Drawing Figures

APPARATUS AND METHOD WHEREBY WAVE ENERGY IS CORRELATED WITH GEOMETRY OF A MANUFACTURED PART OR THE LIKE OR TO POSITIONAL RELATIONSHIPS IN A SYSTEM

This is a continuation-in-part of Ser. No. 911,622, filed June 1, 1978 now Pat. No. 4,200,921; said Ser. No. 911,622 is a division of Ser. No. 679,262, filed Apr. 22, 1976 (now U.S. Pat. No. 4,095,475).

The present invention relates to inspection apparatus and method wherein a sample manufactured part is compared with a standard or master part by impinging wave energy on the standard or master part and deriving information from wave energy reflected from the part, which information is employed to establish a standard against which the sample is compared; it also relates to a system to provide fine-tuning positioning information.

Inspection today is one of the least automated of manufacturing operations which range from simple hand operations to direct numerical contol processes (computer controlled tools). Automated inspection covers the entire gamut of sophistication from hand micrometer inspection to very sophisticated automated inspection stations. However, most shop practice is with hand-operated inspection equipment: very little automation has worked its way into the inspection process.

Automated inspection has been applied most successfully to large production runs. For example, in the manufacture of automobile connecting rods, precision inspection of the machined surfaces is automatic. Because of the large number of nearly identical parts, economics dictate an inspection "transfer line." The inspecting machine is specially designed for each part shape and is generally not computer controlled. While effective for large production runs ($10^6$ parts or more), these techniques are uneconomic for low volume inspection.

Computer controlled inspection machines are most commonly used in automating low production runs. The simplest of these machines has a probe which is brought into contact with various surfaces of the part to be inspected. The part is usually jigged and the probe is positioned by hand. As the probe is touched to various surfaces, a digital readout of the probe's position leads indirectly to the part dimension. The next level of sophistication interfaces a computer to calculate directly the dimensions of the part from the probe's position. The most highly sophisticated inspection machines position the probe under computer or tape control. These are similar to numerically controlled vertical milling machines: the milling machine positions a spinning cutter while the inspection machine positions an inspection probe. Both must be very rigid to minimize stiffness errors. In a numerically-controlled inspection machine, the probe can be positioned with as many as seven degrees of freedom with respect to the machine parts.

Accuracy is an important performance criterion for automated inspection machines. Parts can be inspected to tolerances as small as a 0.0001 inch (2.54 microns), although most machines are somewhat less accurate—0.001 inch (25.4 microns) is typical. Probes which actually contact the part's surface are subject to wear, so non-contact probes are sometimes used. Optical, pneumatic and electronic probes can all measure as accurately as the probe can be positioned, and the part inspected has a maximum dimension on the order one inch to ten inches. Parts whose maximum dimension is either much larger or much smaller than this must be inspected by hand or by specialized inspection machines. However, the vast bulk of machined parts are in the one to ten inch category.

The primary problem of current automated inspection machines is their inability to measure dimensions from a distance. To measure a ten inch part to an accuracy of 0.001 inches (25.4 microns) requires a sensor accurate to one part in 10,000. But this is an order of magnitude greater than the best conventional techniques. For example, optical ranging devices can measure to 0.01 inch (254 microns) from several feet, and electrical sensors can measure to accuracies of 0.001 inch (2.54 microns) but only from distances of about 0.1 inch (0.00254 m). No method is suitable for inspecting from a distance—both 0.001 inch (25.4 microns) accuracy and 10 inch (0.254 m) standoff. Conventional automated inspection machines circumvent this deficiency by moving the sensing probe close to the machined part. Thus, inspecting machines are complicated moving-part devices which are subject to frequent breakdowns if not properly maintained.

Inspection speed is the second important performance criterion of an automated inspection machine. Inertial forces on the massive structure of the inspecting machine prevents rapid inspection. A computer controlled inspecting machine can measure about one dimension a second. Since the various dimensions of a part must be inspected serially (i.e., one dimension after the other) the net result is that even with computer controlled inspection machines, inspection is a time-consuming operation.

Research is being done on several methods to allow rapid inspection from a distance. Electronically manipulated video signals are a low resolution approach. Another intriguing method uses defocused holograms to optically inspect parts. An electronic representation of the holograms is processes to yield dimensional information. Although these techniques appear promising, they have not yet been perfected.

Automated inspection must be viewed with a perspective toward its ultimate use: automated manufacturing or, more specifically, Computer Managed Parts Manufacturing (CMPM) which uses computers to automate the operation of an entire manufacturing plant. Simulations of CMPM systems—few have been built—show that a random part mix gives a manifold increase in productivity. The most efficient operation is not associated with many identical parts which tie up a single machine in the automated factories. Only when all the parts being manufactured simultaneously are substantially different from one another can the true benefits of automated manufacturing be realized.

In a CMPM facility, the parts to be machined are transported on moving pallets. The pallets holding the workpiece can be positioned at each machining station with high accuracy. The palleted workpieces are shuttled by conveyors from one machining station to another under computer control; human operators are required only for monitoring and initial fixturing. The productivity of a CMPM system is substantially increased by (1) 24-hour operation; (2) high utilization of machine tools; (3) elimination of delays between machine operations; (4) elimination of errors by computer management. Inspection is one of the most critical aspects of a CMPM system. When huge factories are automated, malfunction must be recognized very quickly before errors propagate through the entire system. Usually the machined parts cannot wait until their completion to be inspected; they must be periodically inspected through the various machining operations. Hence, more inspection stations are required with more reliance on the results in a CMPM system than in a conventional parts manufacturing factory.

Two types of inspection are required: gross error inspection and dimension inspection. A typical gross error is identifying when a drill bit has been broken off in a partially machined part. Quick error identification is important not only because the bit cannot be used for further drilling, but also because subsequent operation on the part will destroy other cutters. Normally, gross errors are found by the machinist, during or between the machining operations. Since this is not possible on a CMPM system, gross error inspection should be performed after each machining operation. Dimension inspecting, on the other hand, is the high accuracy inspecting of a part's dimension. Generally a part is dimension inspected only after machining is completed. This final inspecting can be used for quality control as well as monitoring tool wear of the various machining operations. Gross error inspecting, then, is low accuracy measurements repeated often, while dimension inspecting is a high accuracy process done seldom.

An automated inspection system to be used in a CMPM system, then, should be capable of inspecting both gross errors and dimensions. The system must accept random part shapes and random sequences. Inspection must be both rapid and accurate. Furthermore, the system should be inexpensive; many inspection stations will be needed in a CMPM system.

Accordingly, an object of the present invention is to provide a method of inspection and apparatus therefor whereby random-shaped parts can be inspected quickly and with acceptable accuracy without need to effect actual physical contact with the part.

Another object is to provide an inspection system in which many identical parts of similar shape can be quickly inspected with regard to geometry.

Still another object is to provide an inspection system that can be used in CMPM-type operations but which is useful, as well, in facilities of a more conventional nature, but facilitates having high volume production of similar parts.

Also, use of automatic assembly equipment is hampered somewhat because of the costly approach now needed to permit final and smaller positioning changes in such equipment. Thus, a still further object is to provide an automatic inspection system which permits feedback in a robot-controlled operation for exact robot manipulation to effect final positioning and similar operations.

These and still further objects are addressed in the description hereinafter.

The foregoing objects are achieved in a method of inspecting manufactured parts and the like (or a method of exact positioning of robot-controlled machines and the like) which employs monochromatic wave energy that is impinged upon and reflected by a part. The wave energy at a single frequency is directed upon a sample part or object which reflects the same. The reflected wave energy is detected and a characteristic of the reflected energy is compared with the same characteristic of a standard or master part similarly treated to note any differences $\theta_A$ therebetween; the difference $\theta_A$ must be within acceptable tolerance in an inspection system. (Or the characteristic of the reflected wave energy is compared with some other wave pattern and information derived from the comparison is used to effect close positioning of the robot-controlled machine.) The wave energy used is acoustic energy and the characteristic of the energy used for comparison is preferably the phase difference between the reflected wave and the original wave that is directed upon the particular part. The wavelength of the acoustic wave energy will vary due to changes in the environment such as, for example, changes in temperature of the air through which the acoustic energy propagates in a typical system employing the present concepts.

The invention is hereinafter described with reference to the accompanying drawing in which.

The present invention is multi-faceted; it applies to a parts inspection system to permit automatic inspection of many like parts; and it applies to a positioning system to permit small, but accurate, positioning corrections. Most of this specification is devoted to the parts-inspection system, but the other aspects are gone into in some detail. The description is first of a general nature and then more specific, the latter being with reference to an actual system built and used to show the efficacy of the present concepts.

Figure 1:
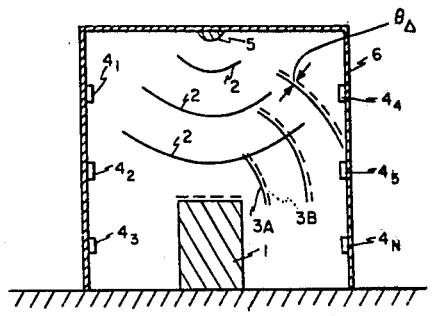
FIG. 1 is a side section view of a schematic representation of a portion of an inspection system that employs the present concepts and shows, among other things, a chamber, microphones and a speaker.
Figure 2:
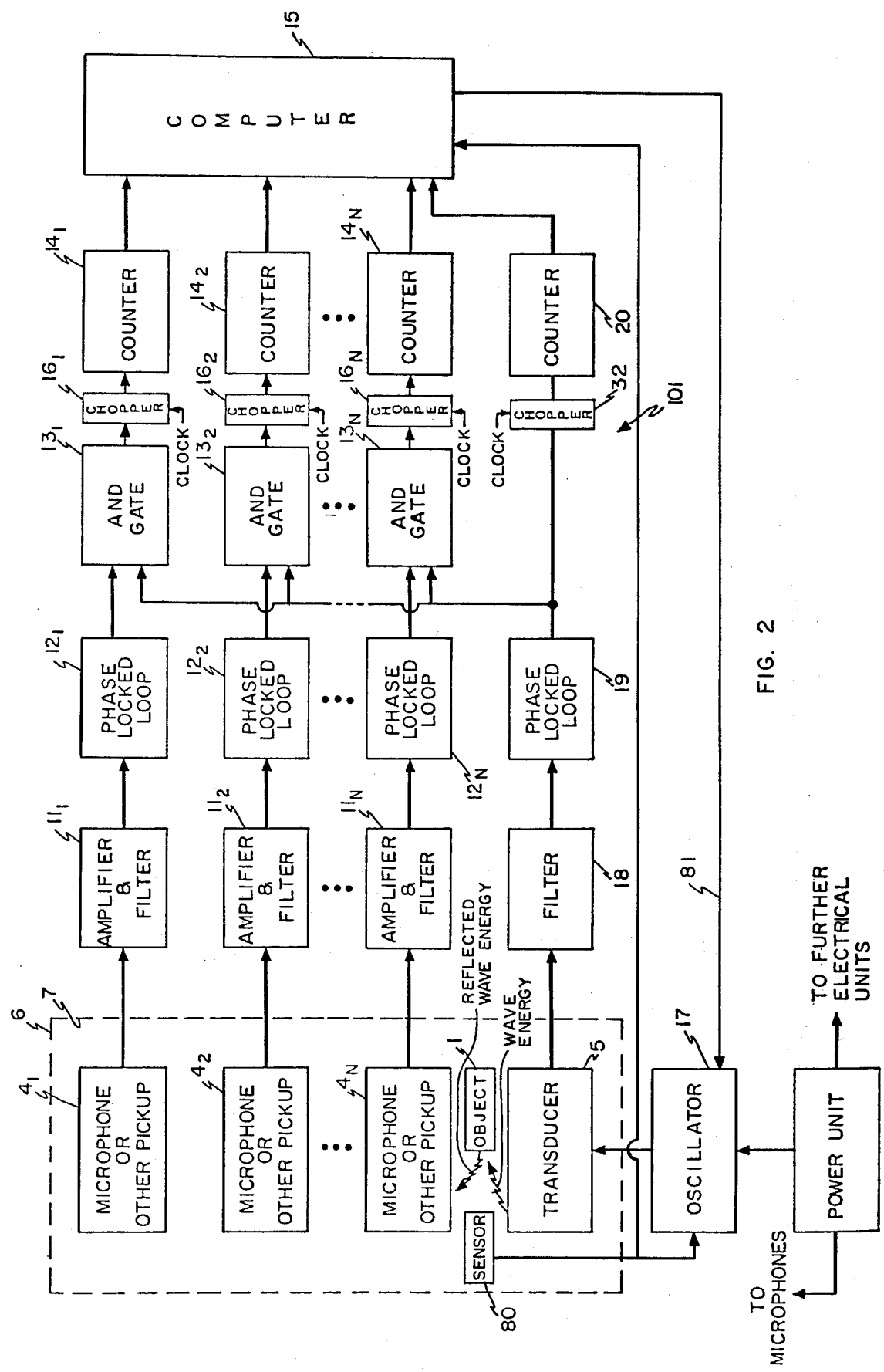
FIG. 2 is a schematic representation, block diagram in form, of an inspection system of the present invention.

Referring now to the figures, apparatus for inspecting manufactured parts and the like is shown at 101 in FIG. 2; the system 101 is acoustic. In FIG. 1 the object labeled 1 is a standard or master part, but it is, for present purposes, a sample part (i.e., a part to-be-inspected), as well, that is, in actual apparatus the system 101 is calibrated using a standard part and, then, the sample part replaces the standard. The solid outer lines of the object 1 represent the dimensions of the standard and the broken upper line represents a sample that has a slightly larger height than the standard, but the same width. Acoustic wave energy as represented by lines 2 is directed upon the object 1 and reflected therefrom. The reflected acoustic wave energy is labeled 3A and 3B (the latter being dotted) to represent the reflected wave energy from the standard part and the sample part, respectively. The space between the waves 3A and 3B represents a phase shift differential and is indicated to be such; that phase shift differential is detected and recorded, as hereinafter explained, and is represented by the designation $\theta_A$ hereinafter. The original wave energy 2 is emitted by an acoustic transducer 5 which may be a speaker and the energy is at a single frequency (i.e., monochromatic). In the preferred form of the invention, the phase of the reflected wave energy 3A is compared with the original wave energy 2 and any phase difference $\theta_B$ therebetween is noted to establish an acceptable standard; for inspection purposes, the phase of the reflected wave energy 3B is compared with the original wave energy 2 and any phase difference $\theta_A$ therebetween is compared with the phase difference $\theta_B$ to determine any differential $\theta_\Delta$ therebetween. A maximum value of the differential $\theta_\Delta$ is established as the value that cannot be exceeded for the sample part to be acceptable. Sensing of the reflected waves is effected by wave receivers or microphones $4_1$.... The part 1, the transducer 5 and the receivers $4_1$... are all housed within a chamber 6. The emitter or speaker 5 sends out waves of a single frequency which are reflected from the part 1 and the interior of the chamber 6 and then picked up by the receivers $4_1$.... It should be noted at this juncture that while, as above indicated, at any instant of time the acoustic energy is monochromatic or single frequency, nevertheless that frequency is changed to maintain constant wavelength of the wave energy despite changes in temperature, the nature of the gas in the chamber 6, and so forth, as noted hereinafter. The electrical circuitry to energize the speaker and the microphones, the analyzing circuitry, etc., are shown in FIG. 2 and are discussed later; but first there is an explanation of the concepts underlying the present invention.

As a result of the single frequency wave emission, the output of the receivers $4_1$... will be sinusoidal signal of the same frequency as the emitted wave but differing in both amplitude and phase. Inspection of the part 1 is possible by monitoring the phase differences between emitted and received waves, as above indicated and as now explained in detail.

First, a master workpiece or standard part 1 is positioned at the inspecting station and enclosed by the inspection chamber. (It should be noted that enclosing the inspection system within the inspection chamber improves the system's sensitivity and reduces extraneous errors, but it is not required; much inspection has been done in open (i.e., unenclosed) environments.) The phase monitored at each receiver, $4_1 \ldots 4_N$, constitutes the phase vector of the master workpiece:

$$\bar{\theta} = (\theta_1, \theta_2, \ldots \theta_N). \tag{1}$$

A subsequent or sample part to be inspected is positioned at the same point and orientation, and a similar phase vector, $$\bar{\theta}' = (\theta'_1, \theta'_2, \ldots \theta'_N) \tag{2}$$

is monitored for the part. The difference in phase between the master workpiece and the part, $$\overline{\Delta\theta} = (\theta_1 - \theta'_1, \theta_2 - \theta'_2, \ldots, \theta_N - \theta'_N) \tag{3}$$

can be used to determine whether a sample part is within tolerances, when it is not, and by how much. (In this description and in the appended claims, the designation $\theta_A$ is used to denote any one of the phase vectors or differences $\theta'_1, \theta'_2 \ldots, \theta_B$ is used to denote any one of the phase vectors or differences $\theta_1, \theta_2 \ldots$, and $\theta_\Delta$ is any differential between $\theta_A$ and $\theta_B$. The major thrust of this specification is the detection of phase differences and comparisons thereof to infer information, be it shape or position, but, as indicated herein, the amplitude or level of the wave energy or some other characteristic thereof can be also used to infer such information and the terms $\theta_A$, $\theta_B$ and $\theta_\Delta$ are intended to embrace the latter as well.) Since automated manufacturing assumes that a part is already mounted on a pallet which can be positioned very accurately, placing the standard part and sample part at the same point and orientation is not difficult.

For gross errors the phase differences may be monitored such that any large change rejects the part. Dimension inspecting, however, is more difficult. A sensitivity matrix S can be determined which gives the sensitivity of each phase difference $\Delta\theta$ for each dimension tolerance on the part. An on-line multiplication of the phase difference vector $(\overline{\Delta\theta})$ times the inverse of the sensitivity matrix results in a deviation vector $\bar{d}$:

$$\bar{d} = (d_1, d_2, \ldots d_m).$$

The deviation vector d is the amount that each dimension of the sample part has deviated from that of the standard part.

$$\bar{d} = S^{-1}\Delta\theta. \tag{5}$$

If any deviation $\bar{d}$ is outside the tolerance for that dimension, the part is rejected. (It will be noted however, that a deviation (called $\Delta d_f$ hereinafter) can originate with an environmental change in the chamber 6, as later discussed in detail.)

The sensitivity matrix assumes linear changes in phase for small deviations: this will be true if the emitted wavelength is much greater than the largest possible deviation. A one-inch (0.0254 m) wavelength allows deviations as large as 0.010 inch (254 microns) to be measured while still satisfying this criterion. The sensitivity matrix itself is determined by a calibration procedure performed only once for each standard part. It involves matching the phase differences $(\overline{\Delta\theta})$ with actual dimensions of parts with high and low tolerance limits. In automated manufacturing, the calibration procedure can be performed under computer control by slightly undercutting or overcutting the various dimensions on the first few parts. Once the sensitivity matrix has been determined, all subsequent parts characterized by the standard part can be inspected online. With off-the-shelf hardware, all dimensions can be simultaneously inspected in less than one second.

Acoustic waves of ten kilohertz are suitable for phase monitored inspection, such waves have a wavelength about one inch long (0.0254 m) and phase can be measured to better than one part in three thousand. Ten kilohertz acoustic waves are in the realm of hi-fi equipment. Although equipment is very cheap, change in acoustic velocity with temperature introduce the inaccuracies into acoustic phase monitored inspection which the present invention serves to mitigate.

The electrical circuitry to accomplish the functions described above is shown in FIG. 2 wherein the chamber 6 is represented by a broken line that encloses the speaker or other transducer 5 and a plurality of microphones or other pickups $4_1 \ldots 4_N$ distributed around the interior of the chamber 6 and operable to detect wave energy reflected from the object 1. Electric signals generated by the pickups $4_1 \ldots 4_N$ are fed to amplifier and filter units $11_1 \ldots 11_N$, respectively, and thence as one input to AND-gates $13_1 \ldots 13_N$, respectively. Another input to the AND-gates is derived from the transducer 5 through a filter 18 and phase locked loop 19. In this way the output of each AND-gate is a pulse whose width represents a phase difference between the reflected wave energy detected by the particular microphone and the original wave energy directed upon the object 1. The outputs of the AND-gates $13_1 \ldots 13_N$ are respectively connected as inputs to choppers $16_1 \ldots 16_N$ which converts the analog signal from the gates to digital signals, the digital signals being fed to counters $14_1 \ldots 14_N$ whose outputs serve as inputs to a computer 15 which can be a general purpose computer properly programmed or a microprocessor. A chopper 32 is connected to receive a signal from the transducer 5 and provide a digital input to a counter 20 that provides a further input to the computer 15. The computer is programmed to provide a difference signal $\theta_A$ for each microphone (i.e., the signals $\theta_1'$, $\theta_2'$ ... before mentioned) by using the respective inputs from the counters $14_1 \ldots$ and comparing each with the input from the counter 20. The computer 15 is further programmed to compare each difference signal $\theta_A$ with a stored difference signal $\theta_B$ (i.e., the signals $\theta_1$, $\theta_2 \ldots$ before mentioned) and to determine any differential $\theta_\Delta$ (i.e., $\theta_1 - \theta_1'$, $\theta_2 - \theta_2' \ldots$) therebetween. In the present context, the elements $4_1$, $11_1$, $12_1$, $13_1$, $16_1$ and $14_1$, for example interact to detect the reflected wave energy and to develop a signal $\theta_A$ therefrom, which signal bears a relationship to geometrical characteristics of the object 1, and the computer 15 serves to compare the signal $\theta_A$ with a standard signal $\theta_B$ representative of the geometrical characteristics of a standard to determine any differential or vector $\theta_{66}$ therebetween. The computer can be programmed to establish limits for the difference $\theta_\Delta$ developed by each pickup on a go-no-go basis. Whereas, for very accurate appraisals for inspecting on the basis of small tolerance limits, phase angle is the characteristic of the single-frequency wave energy that should be used, amplitude or some other characteristic can be employed.

One problem in using the phase monitoring technique is that changes in the medium (e.g., air) through which the acoustic energy moves can adversely affect the resolution. In essence, phase monitoring uses an acoustic wavelength as a standard measuring unit (i.e., yardstick) to measure the dimensions of an object. If the acoustic wavelength changes, it is like trying to measure with a variable-length yardstick. The wavelength changes mostly due to temperature (sound propagates faster in a hotter medium; so for fixed-frequency sound waves, the wavelength also increases in a hotter medium) but it can also change slightly with humidity and velocity of the medium. If a phase-monitoring system were operating in an uncontrolled environment, phase changes would be measured even without changes in the objects undergoing inspection or positioning. These erroneous phase changes limit the resolution of phase measurements. According to the present teachings, such erroneous readings are eliminated or mitigated in the manner now explained.

The effect of these medium changes can generally be reduced two different ways: by (1) open-loop and (2) by closed-loop control. In open-loop control, the changes in the medium are measured by a sensor 80 in FIG. 2, converted to an electrical signal, and fed to the computer 15 along line 82. The computer 15 interprets the changes in the medium and alters the frequency of the emitted acoustic wave energy in such a way as to maintain the fixed acoustic warelength. The frequency is altered by a signal from the computer 15 on line 81 to a voltage-controlled oscillator or the like 17.

For example, if temperature changes in the medium are important, as when the medium is a gas, the temperature can be sensed with a thermocouple. The thermocouple signal can be sent to the computer and the emitted frequency can be changed by the following algorithm for many gaseous media:

$$f = \frac{1}{\lambda} \sqrt{\gamma RT} \tag{6}$$

where f is the emitted frequency, $\lambda$ is the constant wavelength to be maintained, $\gamma$ is the ratio of specific heats for the medium, R is the universal gas constant, and T is the absolute temperature.

The above control of frequency is called open-loop because there is no way of knowing that the frequency change will completely compensate for the changes in the medium. For example, errors in the values of $\gamma$ and R, errors in measuring the temperature T or errors in computation could all contribute to errors in the frequency emitted into the medium. Closed-loop control, on the other hand, does not have these errors. In closed-loop control, phase measurements themselves are used to adjust the emitted acoustic frequency. In the following description, inspection of objects in an inspection chamber 6 in FIG. 2 will be used to illustrate the closed-loop compensation technique.

The phases of the acoustic energy are measured at all microphones $4_1$, $4_2$ ... when no object is in the inspection chamber 6; the resulting phase vector represents the temperature at the time of calibration of the chamber. At any later time when the chamber is once again empty, the frequency can be changed until the same calibration phase vector results.

Because temperature changes usually occur quite slowly, the chamber can be calibrated for temperature between measurements of sample objects. That is, the chamber can be calibrated, a sample object can be placed in the chamber and inspected, and then the object can be removed from the chamber and the frequency adjusted to recalibrate the chamber prior to inspecting the next object. If the objects are measured in fairly quick succession, say once a minute or less, the temperature in the chamber will not have changed enough to introduce significant errors to the inspection process. (Similar techniques can be used to compensate for temperature in a phase monitoring positioning process.)

While compensating an empty chamber (as described above) is often useful, the highest accuracy in phase measurements occurs when the sample object to be inspected is in the inspection chamber during the calibration. Thus, calibration and phase measurement can occur simultaneously. First the sensitivity of each microphone to a known change in the medium must be found with a standard object in the inspection chamber. In the case of temperature or velocity changes, these variables are changed by a known amount and the corresponding phase changes are noted. The sensitivity of each microphone to, say, a temperature change is the temperature change divided by the phase change. A faster but less accurate way of determining the sensitivity of phase to temperature is to quickly change the emitted acoustic frequency by a small amount, giving a corresponding phase change at each microphone due to frequency. The sensitivity then becomes the change in frequency divided by the change in phase.

After the sensitivity of a standard object is found as above explained, similar objects can be simultaneously calibrated for medium changes and inspected by the following procedure. A sample vector object is positioned in the inspection chamber and a first set of phase vector measurements is taken. Each phase vector is multiplied by the sensitivity matrix, which now includes the sensitivity of the medium as one row in the matrix:

$$\begin{bmatrix} \frac{\Delta d_1}{\Delta \phi_1} & \frac{\Delta d_1}{\Delta \phi_2} & \cdots & \frac{\Delta d_1}{\Delta \phi_N} \\ \cdot & \cdot & & \cdot \\ \cdot & \cdot & & \cdot \\ \frac{\Delta d_M}{\Delta \phi_1} & \frac{\Delta d_M}{\Delta \phi_2} & \cdots & \frac{\Delta d_M}{\Delta \phi_N} \\ \frac{\Delta d_f}{\Delta \phi_1} & \frac{\Delta d_f}{\Delta \phi_2} & \cdots & \frac{\Delta d_f}{\Delta \phi_N} \end{bmatrix} \begin{bmatrix} \Delta \phi_1 \\ \Delta \phi_2 \\ \cdot \\ \cdot \\ \Delta \phi_N \end{bmatrix} = \begin{bmatrix} \Delta d_2 \\ \Delta d_2 \\ \cdot \\ \cdot \\ \Delta d_M \\ \Delta d_f \end{bmatrix}$$

where $\Delta d_1 \ldots \Delta d_M$ are changes in the objects geometry from the standard, $\Delta \phi_1 \ldots \Delta \phi_N$ are changes in the phase measurements from the standard, and $\Delta d_f$ is the change in the medium from what is was when the standard was calibrated. If the changes in phase with deviations d are linear or nearly so, the matrix operation assures a reliable estimate of all the deviations. Hence, $\Delta d_f$, the medium change, is known with reasonable accuracy.

To compensate for this medium change, the emitted acoustic frequency can be changed. In the case of temperature changes of the medium, this is particularly true since both frequency and temperature directly affect the emitted wavelength. The frequency is altered in a direction to reduce the medium change. As each new frequency is tried, new phase measurements are made and a new evaluation of the medium change is determined. Eventually, the medium change $\Delta d_f$ can be reduced to some small value such that it has negligible effect on the sample object's inspection. At this point, the frequency has been adjusted so that, despite medium changes, the acoustic wavelength is the same as that of the energy directed on the standard object during calibration. Thus the other deviations, $d_1 \ldots d_M$, are true representations of geometry differences between the object being inspected and the standard object. In practice, these frequency compensation methods were able to reduce phase measurement errors due to medium changes from 40 mrad. to 10 mrad. for open-loop control and to 2 mrad. for closed-loop control.

A less desirable way to compensate for environmental changes in the inspection changes (i.e., open-loop control) is by direct connection from the sensor 80 in FIG. 2 to the frequency controllable oscillator 17. By way of illustration, the sensor 80 can transduce a temperature indication to a voltage which can be used to modify the oscillation frequency of the oscillator 17 and thereby compensate for temperature changes in the chamber 6. In this situation the voltage characteristics of the sensor-transducer 80 and the voltage controlled oscillator 17 are calibrated to provide acceptable compensations. In the various approaches discussed above, the source of the acoustic wave energy is the transducer 5 (energized by the oscillator 17) that emits acoustic energy at a frequency that is adjusted in accordance with the present teachings to maintain a constant wavelength of the acoustic wave energy despite changes in an environmental condition which would otherwise effect changes in said wavelength.

Figure 3:
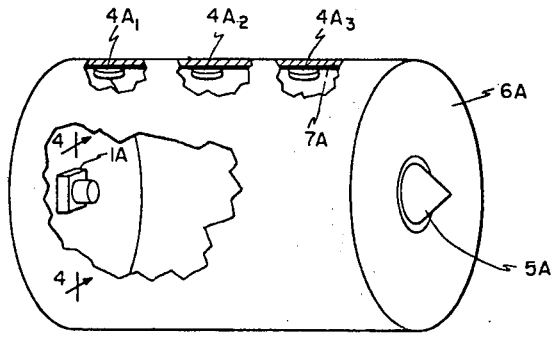
FIG. 3 is an isometric view, partly cutaway, of the same system elements as shown in FIG. 1 but in a slightly different configuration.
Figure 4:
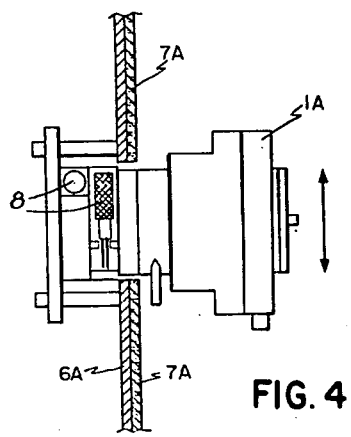
FIG. 4 is an enlarged view taken upon the line 4—4 in FIG. 3 looking in the direction of arrows.

Experimental apparatus was built to verify the feasibility of phase monitored inspection and positioning. FIGS. 3 and 4 show a chamber at 6A with an associated emitter 5A and receivers $4A_1, 4A_2 \ldots$. A ten KHz oscillator is used to drive a speaker through an audio amplifier as before (neither is shown in FIGS. 3 and 4). The receivers are microphones attached to the side of the inspection chamber; the interior has an acoustic absorber surface 7A. After suitable amplification, phase differences between the speaker and the microphones are measured with appropriate electronic circuits. The experiment illustrates phase monitored positioning: the standard object was moved in two directions (i.e., x and y) by calibrated translation stages 8 which are, in fact, stages used in optical systems for accurate translational movement. To ensure that the results are valid for other than simple part shapes, a very complex object was used: an automobile carburetor which is the object marked 1A.

Moving the carburetor 1A slightly in each of two directions ($\Delta x, \Delta y$), caused phase changes ($\Delta \theta_1, \Delta \theta_2$) in each of two microphones. The resulting sensitivity matrix for the two microphones, $$S = \begin{bmatrix} \frac{\Delta \theta_1}{\Delta x} & \frac{\Delta \theta_2}{\Delta x} \\ \frac{\Delta \theta_1}{\Delta y} & \frac{\Delta \theta_2}{\Delta y} \end{bmatrix} = \begin{bmatrix} .06 & -.24 \\ .97 & .01 \end{bmatrix} \quad (8)$$

General  Experimental
expression  data is found by taking the partial derivative of the deviations with respect to each microphone's phase difference.

Given the sensitivity matrix, any movement of the carburetor in the x or y direction can be determined by monitoring the phase differences at each microphone. For instance, if a change in phase of plus two degrees is noted on both microphones, the phase difference vector $\Delta \theta$ will be (2, 2), giving a deviation vector of:

$$\begin{bmatrix} d_x \\ d_y \end{bmatrix} = S^{-1} \cdot \overline{\Delta \theta} = \begin{bmatrix} .04 & 1.05 \\ -4.26 & .26 \end{bmatrix} \cdot \begin{bmatrix} 2.0 \\ 2.0 \end{bmatrix} = \begin{bmatrix} 2 \\ -8 \end{bmatrix} \quad (9)$$

Hence, the carburetor must have moved two mils (fifty-one microns) in the x direction and minus eight mils (203 microns) in the y direction to be consistent with the phase changes recorded by the microphones. This case was purposely chosen so that one microphone would be sensitive to x movement and the other to y movement. In general, this would not be true; both microphones would be sensitive to both x and y movement. By finding the inverse of the sensitivity matrix, the proper linear combination of $\Delta \theta_1$ and $\Delta \theta_2$ can always be found which gives the x or the y movement independently. Usually, more receivers (N) than deviations (M) will exist, hence a pseudo-inverse of the S matrix is appropriate.

Phase monitored inspection was shown to be a valid means for positioning parts of arbitrary shape. The experiments showed that the system is valid for detecting both how much and in which direction an object is out of position.

Automated inspection, as above noted, is currently done by point-by-point inspecting machines. These machines, laden with mechanical or electronic sensors, probe the machined part for any anomalies. The sensors are mechanically moved into close proximity of the sample part since the sensors are only accurate close to the part's surface. (In the present system, on the other hand, the active system elements, the transducers and the pickups $4_1 \ldots$, typically are located several wavelengths (e.g., several inches) from from the part.) Motion in point-to-point machines is controlled by servomotors or stepper motors similar to the motion control in numerically controlled machine tools; however, a sensor replaces the cutter. As each dimension must be inspected one after another by the sensor, the inspection process for each part is necessarily time consuming. A typical part spends many seconds at an inspection station.

Phase monitored inspection is a technique which can greatly increase the speed of automated inspection while simultaneously reducing its cost. The typical part with three or four dimensions to be inspected can be inspected in less than a second with phase monitored inspection. An order of magnitude cost reduction is possible with an acoustic phase monitored inspection system compared to a conventional point-to-point inspection machine. Phase monitored inspection is well suited to automated manufacturing since it easily accepts an arbitrary part shape. No-moving-parts operation reduces maintenance and ensures the long life required in automated factories. Phase monitored inspection is not intrinsically linked to automated manufacturing, as a stand-alone inspection method it is an important advance in the state of the art of automated inspection.

Figure 5:
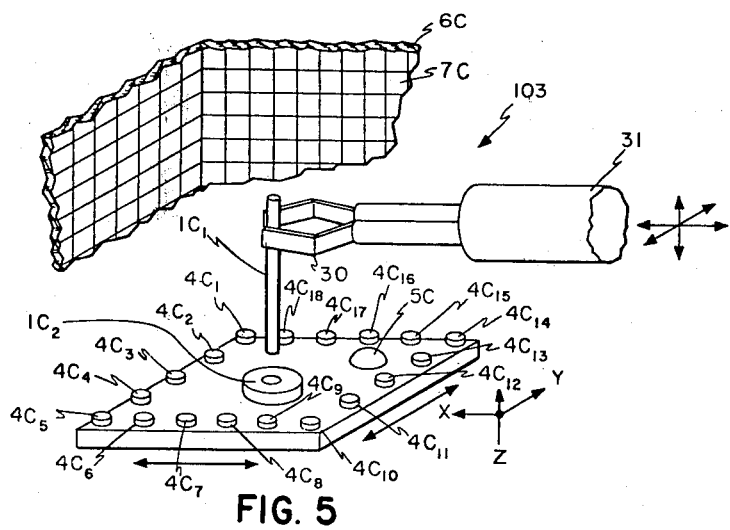
FIG. 5 is an isometric partial view of a system that employs the concepts of the present invention to permit small positional changes in a robot-type device.

The system shown at 103 in FIG. 5 is a part of an automatic assembly system, sometimes called an industrial robot. The duty to be performed in the system 103 is that of fitting a rod $1C_1$ into a central hole in an apertured disk $1C_2$, and the concepts herein disclosed are employed to make final and accurate adjustments of the manipulating hand shown at 30 of an industrial robot 31. It is assumed that gross initial position changes of the hand 30 can be accomplished by other available apparatus. In the system 103 a wave emitter 5C emits wave energy as before and that wave energy is detected by receivers $4C_1$-$4C_{18}$ and appropriately analyzed. Appropriate feedback circuitry permits small changes to be made in the manipulator hand 30 in the x,y and z directions to effect the required assembly. It will be appreciated that what is being done here is that of positioning the object $1C_1$ relative to the source of wave energy 5C, the disk $1C_2$ and the receivers $4C_1 \ldots$ being in known positions relative to the emitter 5C.

Further modifications of the invention herein described will occur to persons skilled in the art and all such modifications are deemed to be within the spirit and scope of the invention as defined by the appended claims.

What is claimed is:

1. Apparatus that comprises, in combination: source means directing acoustic wave energy upon an object that reflects the same, means for detecting the reflected wave energy and developing a signal $\theta_A$ therefrom, which signal $\theta_A$ bears a relationship to geometrical characteristics of the object, means comparing the signal $\theta_A$ with a standard signal $\theta_B$ representative of the geometrical characteristics of a standard to determine any differential $\theta_\Delta$ therebetween, and means for adjusting the frequency of the wave energy to maintain a constant wavelength of the acoustic wave energy despite changes in an environmental condition which would otherwise effect changes in said wavelength.

2. Apparatus as claimed in claim 1 wherein said geometrical characteristics comprise the shape of a sample object which is represented by the signal $\theta_A$ and wherein $\theta_B$ represents the shape of a standard object with respect to which the sample object is compared for purposes of providing tolerance information concerning the sample object.

3. Apparatus as claimed in claim 1 wherein said geometrical characteristics comprise the shape of a sample object, wherein said means for detecting is operable to detect the reflected wave energy at a plurality of separated locations to provide an array of measurements with respect to the object and to develop a signal $\theta_A$ therefrom as to the wave energy detected at each location of said plurality of locations, which signal $\theta_A$ bears a relationship to the shape of the sample, and wherein said means comparing is operable to compare the signal $\theta_A$ derived from each location with a standard signal $\theta_B$ representative of the shape of a standard object with which the sample object is compared for purposes of providing tolerance information concerning the sample object to determine any differential $\theta_\Delta$ between $\theta_A$ and $\theta_B$ for each location to provide an array of differentials $\theta_\Delta$ and which includes means for combining the array of differentials $\theta_\Delta$ with an array of sensitivities to produce an array of deviations d, each deviation d being produced by a plurality of said differentials $\theta_\Delta$.

4. Apparatus as claimed in claim 3 adapted to produce one deviation $\Delta d_f$ which is a function of temperature, the temperature deviation $\Delta d_f$ thus produced being connected as input to the source means to effect adjustment of said frequency.

5. Apparatus as claimed in claim 1 in which the environmental condition is temperature and which includes means to sense the temperature and to create an electrical signal representation of said temperature, said electrical signal being connected as input to the source means to effect changes in the frequency of the wave energy.

6. Apparatus as claimed in claim 1 in which the acoustic wave energy is substantially monochromatic in which the environmental condition is temperature, changes in temperature acting to change the wavelength of the acoustic wave energy, in which the signal $\theta_A$ is developed by comparing the phase of the reflected wave energy with the phase of the wave energy directed upon the object, $\theta_A$ being any phase difference between the phase of the reflected wave energy and the phase of the wave energy being directed upon the object.

7. A method that employs the geometrical characteristics of an object as a source of information with respect to the object, that comprises: directing acoustic wave energy upon an object that reflects the same; detecting the reflected wave energy and developing a signal $\theta_A$ therefrom, which signal $\theta_A$ bears a relationship to geometrical characteristics of the object, comparing the signal $\theta_A$ with a standard signal $\theta_B$ representative of the same geometrical characteristics of a standard to determine any differential $\theta_\Delta$ therebetween, and adjusting the frequency of the acoustic wave energy to maintain a constant wavelength of the acoustic wave energy despite changes in a environmental condition which would otherwise effect changes in said wavelength.

8. A method as claimed in claim 7 in which the environmental condition is temperature and which includes sensing the temperature and creating an electrical signal representation of said temperature, said electrical signal being the being used to effect changes in the frequency of the wave energy.

9. A method as claimed in claim 7 in which the acoustic wave energy is substantially monochromatic wave energy whose wavelength is affected by temperature deviations, in which said environmental condition is the temperature of a fluid through which the wave energy propagates, and which includes comparing the phase of the reflected wave energy with the phase of the acoustic wave energy directed upon the object, the signal $\theta_A$ being any difference in phase between the two.

* * * * *